(12) United States Patent
Welles et al.

(10) Patent No.: US 9,436,931 B2
(45) Date of Patent: Sep. 6, 2016

(54) REMOTE PROMPTING INFRASTRUCTURE

(75) Inventors: Devon Welles, Hillsboro, OR (US); Chris Gough, Portland, OR (US)

(73) Assignee: INTEL CORPORATION, Santa Clara, CA (US)

( * ) Notice: Subject to any disclaimer, the term of this patent is extended or adjusted under 35 U.S.C. 154(b) by 2095 days.

(21) Appl. No.: 11/529,575

(22) Filed: Sep. 29, 2006

(65) Prior Publication Data
US 2008/0082404 A1  Apr. 3, 2008

(51) Int. Cl.
| | |
|---|---|
| *G06Q 10/10* | (2012.01) |
| *G06Q 30/00* | (2012.01) |
| *H04L 12/28* | (2006.01) |
| *G06Q 30/02* | (2012.01) |
| *H04L 12/58* | (2006.01) |
| *H04L 29/08* | (2006.01) |

(52) U.S. Cl.
CPC ............ *G06Q 10/107* (2013.01); *G06Q 10/10* (2013.01); *G06Q 30/0251* (2013.01); *G06Q 30/0267* (2013.01); *H04L 12/2827* (2013.01); *H04L 12/58* (2013.01); *H04L 67/26* (2013.01); *H04L 2012/285* (2013.01)

(58) Field of Classification Search
CPC ............ G06Q 30/0251; G06Q 30/02; G06Q 30/0267; H04L 12/2827
USPC ............................... 705/10, 14, 14.49, 14.64
See application file for complete search history.

(56) References Cited

U.S. PATENT DOCUMENTS

| | | | | |
|---|---|---|---|---|
| 3,925,763 | A * | 12/1975 | Wadhwani et al. | ........... 340/538 |
| 5,898,831 | A * | 4/1999 | Hall et al. | ........................ 726/3 |
| 6,088,659 | A * | 7/2000 | Kelley et al. | .................... 702/62 |
| 6,121,593 | A * | 9/2000 | Mansbery et al. | ............ 219/679 |
| 6,867,697 | B2 * | 3/2005 | Nanayakkara et al. | ... 340/573.1 |
| 6,906,635 | B1 * | 6/2005 | Moutaux et al. | ........ 340/825.22 |
| 7,006,881 | B1 * | 2/2006 | Hoffberg et al. | ............... 700/83 |
| 7,043,532 | B1 * | 5/2006 | Humpleman et al. | ........ 709/208 |
| 7,119,689 | B2 * | 10/2006 | Mallett et al. | ............. 340/572.1 |
| 7,181,438 | B1 * | 2/2007 | Szabo | ............................. 707/2 |
| 7,242,988 | B1 * | 7/2007 | Hoffberg et al. | ............... 700/28 |
| 7,244,231 | B2 * | 7/2007 | Dewing et al. | ............... 600/300 |
| 7,305,350 | B1 * | 12/2007 | Bruecken | .......................... 705/1 |
| 7,420,474 | B1 * | 9/2008 | Elks et al. | .................... 340/678 |
| 7,562,304 | B2 * | 7/2009 | Dixon et al. | .................. 715/738 |

(Continued)

OTHER PUBLICATIONS

Microsoft Press, One Microsoft Way, Redmond, Washington 98052-6399; Computer Dictionary Second Edition; ISBN 1-55615-597-2; Casey D. Doyle et al.; Copyright 1994.*

*Primary Examiner* — Amanda Abrahamson
*Assistant Examiner* — Scott C Anderson
(74) *Attorney, Agent, or Firm* — Pillsbury Winthrop Shaw Pittman LLP

(57) ABSTRACT

The invention relates to a method and apparatus for sending and receiving prompts to end-users inside and outside the home. A prompt, for example, a message, image, or sound is presented to the end user in order to notify them of a health event, serve as a simple reminder, helps them through their daily activities. The invention includes, for example, the following components: a remote prompting client which runs on the end-user's home network and is typically associated with a physical display device. This entity has the ability to receive a prompt request from a remote prompting host, and display the prompt to the end-user; and a remote prompting host which runs on the end-user's home network and has the ability to scan the network and discover all existing remote prompting clients.

18 Claims, 7 Drawing Sheets

(56) References Cited

U.S. PATENT DOCUMENTS

| | | | |
|---|---|---|---|
| 7,650,425 B2* | 1/2010 | Davis et al. | 709/238 |
| 7,653,394 B2* | 1/2010 | McMillin | 455/444 |
| 8,225,194 B2* | 7/2012 | Rechsteiner et al. | 715/206 |
| 8,464,278 B2* | 6/2013 | Nesamoney et al. | 719/318 |
| 8,725,567 B2* | 5/2014 | Huang et al. | 705/14.49 |
| 2002/0150147 A1* | 10/2002 | Liang | 375/133 |
| 2003/0014283 A1* | 1/2003 | Iwano et al. | 705/3 |
| 2003/0037072 A1* | 2/2003 | Bowman et al. | 707/201 |
| 2003/0109938 A1* | 6/2003 | Daum et al. | 700/11 |
| 2003/0163372 A1* | 8/2003 | Kolsy | 705/14 |
| 2003/0184441 A1* | 10/2003 | Nanayakkara et al. | 340/573.1 |
| 2004/0015385 A1* | 1/2004 | Kumakawa | 705/9 |
| 2004/0057340 A1* | 3/2004 | Charles-Erickson et al. | 368/10 |
| 2004/0064351 A1* | 4/2004 | Mikurak | 705/7 |
| 2005/0021779 A1* | 1/2005 | Ahamed et al. | 709/229 |
| 2005/0065813 A1* | 3/2005 | Mishelevich et al. | 705/2 |
| 2005/0138137 A1* | 6/2005 | Encarnacion et al. | 709/217 |
| 2005/0138179 A1* | 6/2005 | Encarnacion et al. | 709/227 |
| 2005/0138192 A1* | 6/2005 | Encarnacion et al. | 709/230 |
| 2005/0138193 A1* | 6/2005 | Encarnacion et al. | 709/230 |
| 2005/0197865 A1* | 9/2005 | Jordan | 705/3 |
| 2005/0222933 A1* | 10/2005 | Wesby | 705/36 |
| 2006/0010199 A1* | 1/2006 | Brailean et al. | 709/204 |
| 2006/0020366 A1* | 1/2006 | Bloom | 700/226 |
| 2006/0034156 A1* | 2/2006 | Chen | 368/10 |
| 2006/0036619 A1* | 2/2006 | Fuerst et al. | 707/100 |
| 2006/0111933 A1* | 5/2006 | Wheeler | 705/2 |
| 2006/0122864 A1* | 6/2006 | Gottesman et al. | 705/2 |
| 2006/0125620 A1* | 6/2006 | Smith et al. | 340/506 |
| 2006/0135156 A1* | 6/2006 | Malu et al. | 455/432.3 |
| 2006/0136142 A1* | 6/2006 | Berlin et al. | 702/20 |
| 2006/0136259 A1* | 6/2006 | Weiner et al. | 705/2 |
| 2006/0179313 A1* | 8/2006 | Wang | 713/170 |
| 2006/0200253 A1* | 9/2006 | Hoffberg et al. | 700/19 |
| 2007/0118399 A1* | 5/2007 | Avinash et al. | 705/2 |
| 2007/0169194 A1* | 7/2007 | Church et al. | 726/23 |
| 2007/0197261 A1* | 8/2007 | Humbel | 455/558 |
| 2007/0293952 A1* | 12/2007 | Callaghan et al. | 700/9 |
| 2008/0008125 A1* | 1/2008 | Pham et al. | 370/329 |
| 2008/0082404 A1* | 4/2008 | Welles et al. | 705/14 |
| 2008/0103608 A1* | 5/2008 | Gough et al. | 700/1 |
| 2008/0262872 A1* | 10/2008 | Perry et al. | 705/3 |
| 2009/0070149 A1* | 3/2009 | Kurian et al. | 705/3 |
| 2009/0077601 A1* | 3/2009 | Brailean et al. | 725/109 |
| 2009/0248182 A1* | 10/2009 | Logan et al. | 700/94 |
| 2010/0268605 A1* | 10/2010 | Waelbroeck et al. | 705/14.53 |
| 2011/0145731 A1* | 6/2011 | Anderson et al. | 715/760 |
| 2013/0117395 A1* | 5/2013 | Bushmitch et al. | 709/206 |

* cited by examiner

| Transducer Bridge Software | |
|---|---|
| ZWave-UPnP Bridge | |
| Bluetooth-UPnP Bridge | |
| UPnP 1.0 Microstack | |
| Intel PCB | |
| Serial (57.6 kbps) | |
| Serial/USB Interface for additional controller | |
| Z-Wave Module (ZM2102) | Serial Interface |
| Gumstix connex 400xm-bt | |
| OS: Linux (2.6.11), uboot-bootloader | |
| Memory: 64MB SDRAM 16 MB Strataflash - xtended memory | |
| *WiFi: Gumstix cfstix module (compact flash) | |
| Bluetooth: Infineon Module (ROK104001) | |
| Processor: Intel XScale® PXA255 400MH | |
| Debug: USB Client / Console Serial Port | |

*Alternatively, we could use etherstix for 10/100 support

FIGURE 2

REMOTE PROMPTING INFRASTRUCTURE

FIELD OF INVENTION

The invention relates to a method and apparatus for sending and receiving prompts to end-users, and in particular, to end-users located in a home.

BACKGROUND

Currently, many elder adults rely on a variety of low-tech methods to remember important events such as handwritten messages posted throughout the home. Concerned family members must visit/phone frequently to gather this type of information which is problematic for the elder adult (they don't want to be a burden on their family members) as well as the family caregiver (feelings of guilt for not calling/visiting often enough).

Personal health has been targeted as one of the major growth areas for the foreseeable future. Elder care is likely to be one of the primary (future) use cases in this area. A remote prompting infrastructure interoperable with a wide variety of devices that can inform elder adults and remote caregivers of critical/non-critical health events is going to be a key building block that will enable elder care related solutions in the home.

Currently there is no advertising tied into the prompting systems out there. By associating a relevant ad with a specific prompt to each individual user, the effectiveness of the ads is increased. Also, since the ad is tied to a prompt that the user needs to see, then the ad will be seen too.

There are ads that are associated with gross classifications like television audience, and there are targeted ads that are associated with finer classifications like web-browsing choices, but neither of these are delivered in conjunction with a prompt that the user needs to comprehend and respond to, nor do they guarantee that the user will see them.

BRIEF DESCRIPTION OF THE DRAWINGS

FIG. 2 illustrates an exemplary Transducer Access Point architecture.

DETAILED DESCRIPTION

Figure 1:
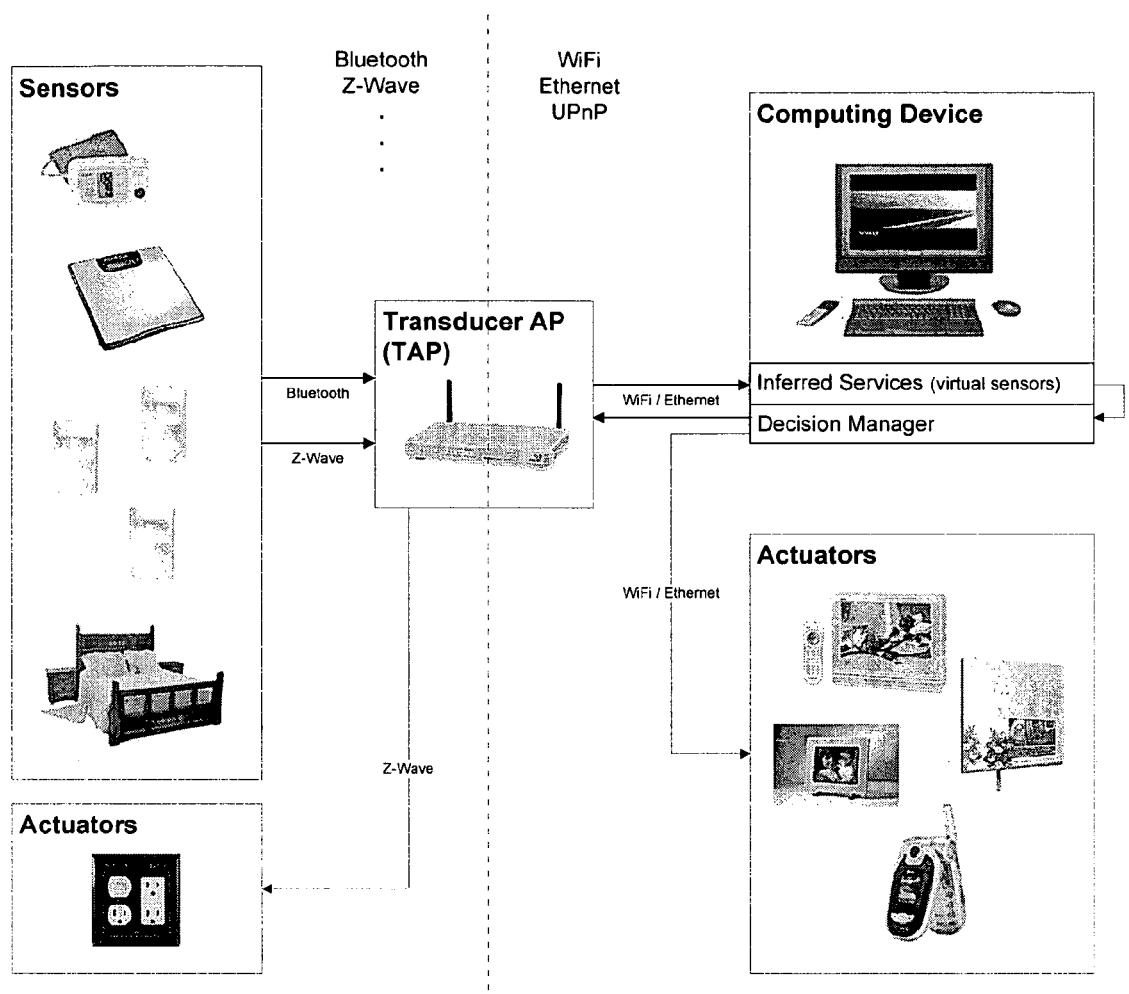
FIG. 1 illustrates a high-level platform architecture.

The embodiment of the invention relates to a system for sending prompts to a user in a network including at least one remote prompting client to receive a prompt and notify the user of an event and a remote prompting host to scan the network to detect the at least one remote prompting client, wherein the remote prompting host identifies an event of the user and sends the prompt to the detected at least one remote prompting client. Preferably, the remote prompting host is hardware and/or software running on a computer which interfaces with sensors located throughout the network to determine the event of the user. Preferably, the remote prompting client is a module on the user's network associated with at least one of a network display device, television, phone, cell phone, picture frame display, and mirror. According to a further embodiment, the prompt is at least one of a message, image and sound. Preferably, an advertisement is paired with the prompt and/or the advertisement is loaded to the remote prompting host. According to yet another embodiment, the remote prompting host determines when the advertisement is paired and sent with the prompt based on the event, sends the advertisement with the prompt, and notifies a central server responsible for the advertisement that the advertisement was sent and displayed at the user's network.

According to yet another embodiment, a method is provided for receiving a prompt at a remote prompting client and notifying the user of an event and scanning the network at a remote prompting host to detect the at least one remote prompting client, wherein the remote prompting host identifies an event of the user and sends the prompt to the detected at least one remote prompting client. Preferably, the remote prompting host is hardware and/or software running on a computer which interfaces with sensors located throughout the network to determine the event of the user. Preferably, the remote prompting client is a module on the user's network associated with at least one of a television, phone, cell phone, picture frame display, and mirror. According to a further embodiment, the prompt is at least one of a message, image and sound and/or an advertisement is paired with the prompt. In another embodiment, the advertisement may be loaded to the remote prompting host.

According to this embodiment, the remote prompting host determines when the advertisement is paired and sent with the prompt based on the event, sends the advertisement with the prompt, and notifies a central server responsible for the advertisement that the advertisement was sent and displayed at the user's network.

According to a further embodiment, a system is provided for monitoring a user in a network, the system including a sensor/actuator network to determine when an event occurs in the system, a computing device to monitor and prompt the system when an event occurs, the computing device including an inference engine and a decision manager, a prompting device to receive prompts from the computing device and for displaying the prompt to the user, and a gateway or transducer access point to bridge the sensor/actuator network with the computing device.

Preferably, when the sensor/actuator network determines that an event has occurred, sending a response to the computing device. According to this embodiment, when the computing device receives the response, the inference engine analyzes the response and the decision manager initiates actuation of the associated prompting device. Preferably, the inference engine collects and interprets the response in order to analyze data sent from the sensor/actuator, and the decision manager initiates actuation of the associated prompting device based on rules defined by the system.

FIG. 1 illustrates high-level platform architecture. The "left-side" of the diagram is characterized by low-power, in some cases proprietary protocols, used by the sensors and actuators to handle communications. The "right-side" of the diagram represents the Digital Home, where WiFi, Ethernet, and UPnP are the communication technologies of choice. The "Healthy Digital Home" is enabled (in part) by the Transducer Access Point (TAP), which bridges the various sensor/actuator networks (specifically Bluetooth and Z-Wave in this case), to WiFi/Ethernet, and exposes the various physical devices "on the left" as UPnP devices "on the right" such that intelligent control points can perform actions, request state, and subscribe to event notifications.

UPnP is an architecture for pervasive peer-to-peer network connectivity of intelligent appliances, wireless devices, and PCs. It is designed to bring easy-to-use, flexible, standards-based connectivity to ad-hoc or unmanaged networks whether in the home, in a small business, public spaces, or attached to the Internet. UPnP is a distributed, open networking architecture that leverages TCP/IP and the Web technologies to enable seamless proximity networking in addition to control and data transfer among networked devices in the home, office, and public spaces.

UPnP is more than just a simple extension of the plug and play peripheral model. It is designed to support zero-configuration, "invisible" networking, and automatic discovery for a breadth of device categories from a wide range of vendors. This means a device can dynamically join a network, obtain an IP address, convey its capabilities, and learn about the presence and capabilities of other devices.

Protocols supported by the TAP include, for example, Bluetooth and Z-Wave. Obviously, any protocol may be used as would be appreciated by the skilled artisan. The protocols tend to be flexible, extensible building blocks that allows radio protocols such as these to communicate with other devices inside and outside the home.

The following sensors and actuators are examples of devices that may be integrated into the platform: Scales, Blood Pressure Monitors, Pressure Sensors, Presence Sensors, Multi-Level Light, Television, Personal Computers, Bathroom Mirror Displays, Picture Frame Displays, Cell Phones, PDAs, etc. Again, this list of devices is exemplary and not exclusive. Due to limitations exhibited by typical wireless sensors (e.g. power profile, transmission range, memory capacity, cost, etc.) a TAP is used to allow communication to take place, as described above. FIG. 2 illustrates an exemplary TAP Architecture. The TAP is intended to serve as a proxy for the low-powered (Bluetooth and Z-Wave) transducers.

An Inference Engine is the computational entity responsible for computing and understanding the data collected from the home sensor network. Essentially, sensor data is collected, and compared against a probabilistic model in order to determine the events that the data represents. Based on the recognized events, the decision manager may initiate local and/or remote actuation. For example; the probabilistic model may determine, based on data collected from multiple sensors (e.g., bed pressure sensor, motion sensors, bedroom door contact switch, etc.) that the occupant is in bed.

Figure 3:
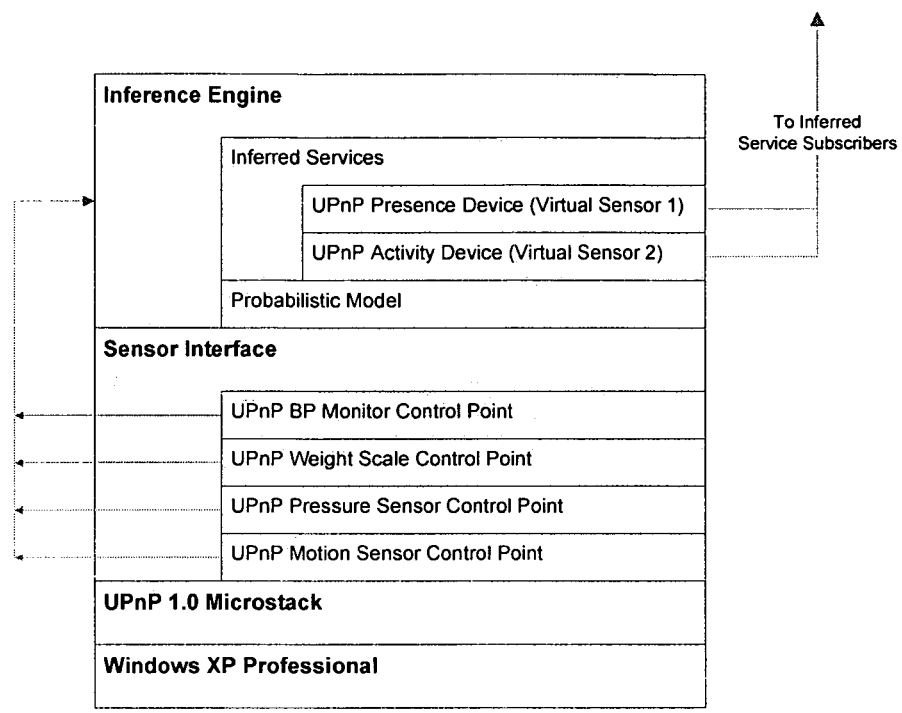
FIG. 3 illustrates the inferred services architecture of the system.

In FIG. 3, a Sensor Interface is the block responsible for communicating with devices exposed by the TAP. This "raw" sensor data is collected and interpreted by the inference engine. The external interface to the inference engine is referred to as Inferred Services. Inferred Services are exposed as devices and are indistinguishable from their physical counterparts on the home network. In this way, Inferred Services can be thought of as "virtual sensors" that leverage the processing power of a computing device to increase the accuracy associated with the data they are transmitting, as well as collating disparate information from various sensors to represent higher level events. For example: The Activity Device depicted in FIG. 3 may utilize data from a multitude of sensors (e.g., motion, light, contact switches, RFID, time of day, etc.) to determine that the home occupant is making breakfast. Interested control points may subscribe to the "making breakfast" event in the same manner they would use to communicate with a specific physical sensor device.

Figure 4:
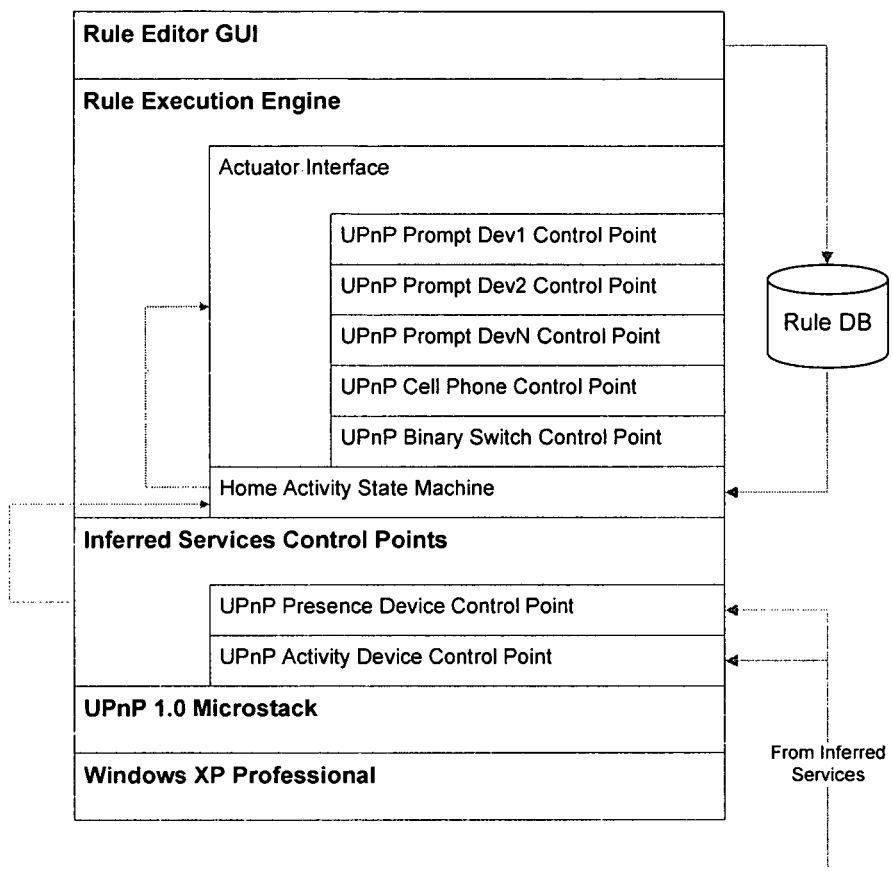
FIG. 4 illustrates the device manager architecture of the system.

A Decision Manager, illustrated in FIG. 4, is an example of a general control point that subscribes to the Inferred Services. Based on event notifications received from the Inferred Services, and rules defined by users of the system, actuation is initiated either inside or outside the home environment. The Inferred Services Control Points block is the interface into the Inferred Services. In this example, both the Inferred Services and Decision Manager reside in the same computing device, but this is not a requirement of the system (nor is having one distinct set of Inferred Services and one distinct Device Manager). One characteristic about the system is the following: If the underlying set of physical sensors change, while the events subscribed to may be more (or less) accurate, there is no need for the Decision Manager to change.

The information retrieved from Inferred Services in conjunction with user-defined rules will be used within the framework of the platform to construct a state machine representing the activities taking place in the home. The following is an example of the Decision Manager in action:

1. Remote family caregiver accesses rule editor via web interface;
2. RFC creates a rule that specifies the following: If primary occupant is in the bathroom for over 2 hours, send SMS message to my cell phone;
3. Occupant enters bathroom (detected by motion sensor and/or weight scale measurement); and
4. 2 hours elapse (an unusually long time for the home occupant to remain in the bathroom), state machine raises alert to Rule Execution Engine, and SMS message is sent via actuator interface alerting the remote caregiver of a possible fall.

For the purposes of this example, the following types of actuation will be supported by the Decision Manager's Actuator Interface:

Prompt, including text and color (to designate severity) overlaid on:
Television
Picture Frame
Bathroom Mirror Display (in addition to 'text', the bathroom mirror will have a more sophisticated display combining the most recent weight scale measurement and a graphical depiction of measurement history).
Cell Phone (SMS message)
(Z-Wave) Light switch on/off (to show communication backchannel through the TAP).

It is readily understood that the above-mentioned types of actuation is not limiting, but rather exemplary.

Figure 5:
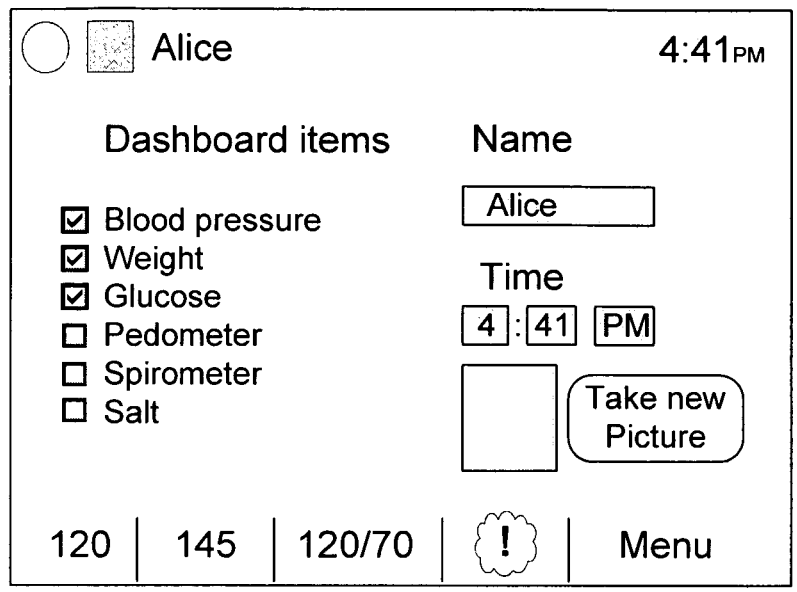
FIG. 5 illustrates an exemplary display setting for a graphical user interface.
Figure 6:
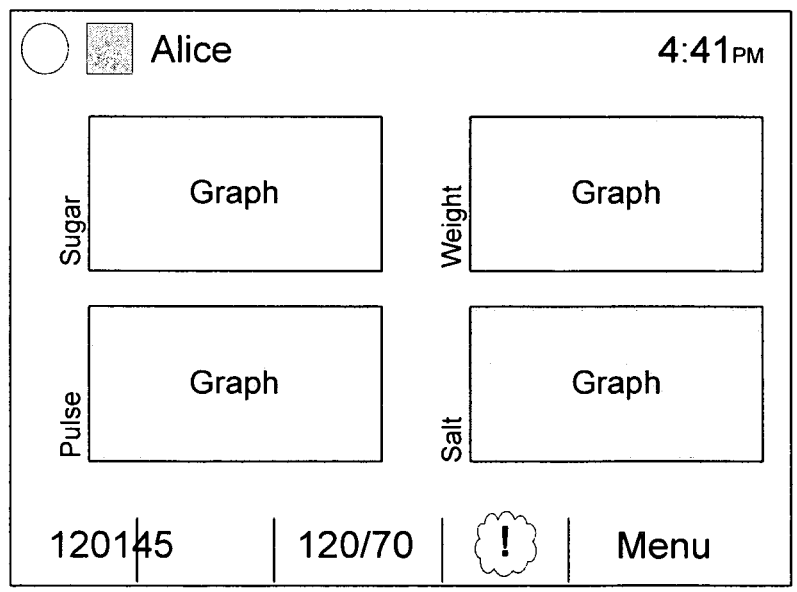
FIG. 6 illustrates an exemplary history for a graphical user interface.

FIGS. 5 and 6 are exemplary user interfaces. FIG. 5, for example, illustrates a display setting for a graphical user interface, while FIG. 6 illustrates the history of a graphical user interface.

There exist many reminder or prompting systems on computers or entertainment systems. Some examples are calendar applications that remind you to go to a meeting or appointment, or a digital video recorder that prompts you to change the channel to a show that's on.

Future prompting systems may be more intelligent and display prompts for users on one of many displays in the house based on the nature of the prompt or the location of the person. Such a system would have knowledge of the nature of the prompt (medical, entertainment, etc) and the location of the person in their home.

This invention, in another exemplary embodiment, may also use the remote prompting infrastructure to deliver a targeted ad to an individual that is guaranteed to be seen because it is tied in with the prompt. The ad and prompt can be shown continuously until the prompt is acknowledged. Also, since the remote prompting infrastructure will have some knowledge of the user, advertisers can filter the type of individual they'd like to target by age, hobbies, or location.

Some Examples:

A prompt pops up on the TV reminding a person that they need to refill their prescriptions. At the same time an ad is displayed for a local pharmacy at which the prescription can be filled.

A graph is displayed on the bathroom mirror of a person's weight and blood pressure. Shortly afterwards the mirror displays an ad for a local health food store.

A reminder comes up for a person to go to a doctor's appointment to see how their medications are working. At the same time an ad is displayed for a competing medication with different side effects or perhaps a generic brand that is cheaper. This way the person has the new medication fresh in their mind for the appointment.

Figure 7:
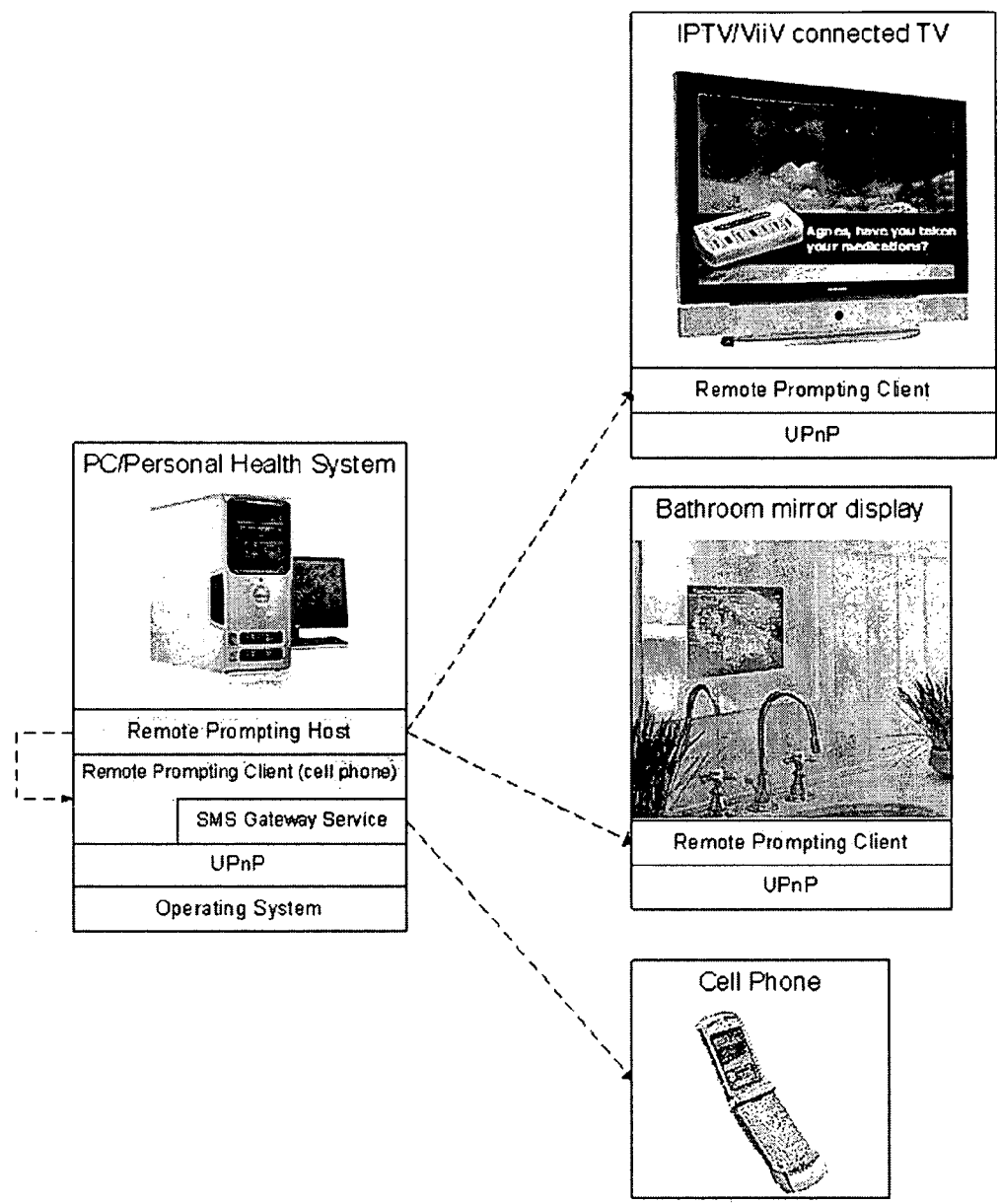
FIG. 7 illustrates an exemplary remote prompting infrastructure in accordance with the invention.

FIG. 7 illustrates an exemplary remote prompting infrastructure. This infrastructure, in use with the above described system, discloses a method and apparatus for sending and receiving prompts to end-users inside and outside the home where prompt is defined as; a message, image, or sound (or some combination of the three) presented to the end user in order to; notify them of a health event, serve as a simple reminder, help them through their daily activities (e.g. an elder adult with mild cognitive decline). The invention includes the following components:

Remote Prompting Client:

This is a software and/or hardware module that is running on the end-user's home network and are typically associated with a physical display device (e.g. television, cell phone, picture frame display, bathroom mirror with integrated TV, etc.). This entity has the ability to receive a prompt request from a Remote Prompting Host, and display (either visually, audibly or by touch) the prompt to the end-user.

Remote Prompting Host:

This is a software and/or hardware module that is running on the end-user's home network and has the ability to scan the network and discover all existing Remote Prompting Clients. The Remote Prompting Host performs two critical functions:

Interface to sensor/medical device network to determine where the end-user is and what they are doing Send prompt to appropriate Remote Prompting Client to notify the local/remote user of critical or non-critical health events, reminders, Activities of Daily Living (ADL) assistance, etc.

Example:

Agnes is an elder adult with type II diabetes.

Agnes hasn't measured her weight or blood pressure in several days.

Because her weight scale and blood pressure monitor are both connected to her personal health system, the system is aware of this.

Agnes is sitting on her couch watching TV.

The system uses a pressure sensor in the couch and power clamp on the television to recognize this activity.

The Remote Prompting Host via its interface to the sensor network knows that Agnes has not measured her weight or blood pressure recently and that she is watching TV.

The Remote Prompting Host sends a prompt to the Remote Prompting Client associated with the television and a message/icon is overlaid on top of the TV signal informing Agnes that she needs to measure her weight and blood pressure, for example using a network laptop connected to the TV, or an IPTV or living room PC.

Agnes presses a button on her remote control to clear the prompt; the system is now aware that she has seen it.

Agnes measures her weight and blood pressure during the next commercial (otherwise, she could/would be prompted again at some point in the future).

Agnes has lost a significant amount of weight since her last weight measurement.

The Remote Prompting Host sends a prompt to the Remote Prompting Client associated with Agnes' daughter's cell phone. An SMS message is sent to her daughter's cell phone (via an Internet based SMS gateway service) informing her daughter of this potentially dangerous health event.

The remote prompting is part of a larger platform (i.e. architecture) that is responsible for, in addition to the remote prompting, all other aspects associated therewith.

Figure 8:
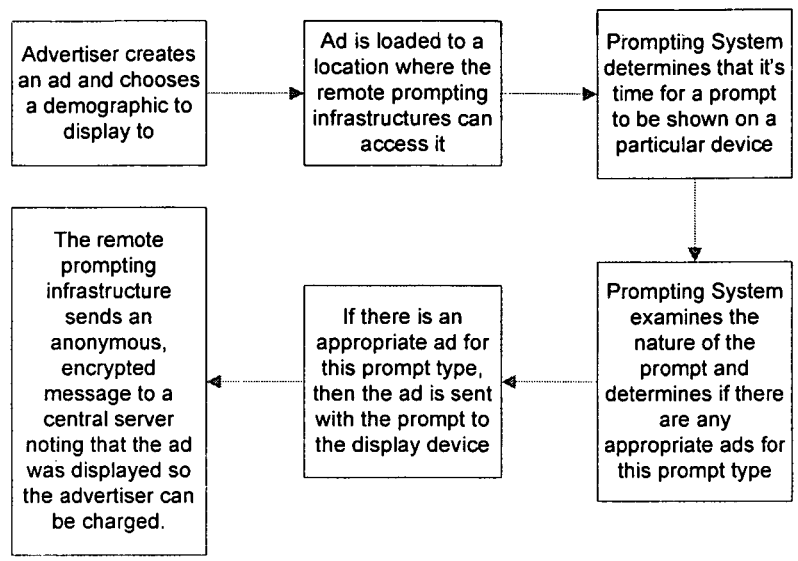
FIG. 8 is a flow diagram of pairing an advertisement with a remote prompting in accordance with the invention.

FIG. 8 is a flow diagram of pairing an advertisement with a remote prompting in accordance with the invention. This invention would ensure that advertisements are hitting a targeted and relevant market by pairing the ad with a prompt that a person receives through a remote prompting infrastructure. Since the prompt would necessarily be specific to the person (take your medication, etc), an appropriate ad to that same person would have a much higher likelihood of success. It also guarantees that the ad is seen by the target individual. This method also can protect the privacy of the people receiving the ads from the advertisers.

This invention also increases the attractiveness of remote prompting infrastructures to service providers by creating another revenue stream.

It is readily understood by the skilled artisan that the embodiments disclosed herein are merely exemplary and are not intended to limit the scope of the invention.

What is claimed is:

1. A system comprising:
a sensor;
a remote prompting host;
first and second remote prompting clients;
a first network configured to communicate with:
the sensor configured to collect data related to an event associated with a user, wherein the sensor is configured to support a first wireless protocol operational in sub-gigahertz frequency range providing a data rate of upto 100 kbps;
a bridge device to bridge wireless communication based at least on the first wireless protocol at the sensor and wireless communication based at least on an Ethernet protocol at the remote prompting host; and
the remote prompting host comprising one or more hardware modules configured to:
receive, from the sensor via the bridge device, the data collected by the sensor; and
based on the event identified based on the received data and a predefined rule, generate and transmit a prompt related to the identified event, wherein the prompt includes information about the identified event and an action responsive to the identified event; and
a second network configured to communicate with:

the first remote prompting client arranged in communication with the remote prompting host operating on the first network and configured to receive the prompt from the remote prompting host and present the received prompt to the user via a physical device associated with the first remote prompting client; and the second remote prompting client arranged in communication with the remote prompting host and configured to receive a notification from the remote prompting host and present the notification to another user, the notification indicating at least that the user has received the prompt associated with the identified event.

2. The system of claim 1, wherein the sensor is located within the first network.

3. The system of claim 1, wherein the first remote prompting client, the second remote prompting client, or both are associated with at least one of a network display device, television, phone, cell phone, picture frame display, and mirror on the first network.

4. The system of claim 1, wherein the prompt is at least one of a message, image and sound.

5. The system of claim 1, wherein an advertisement is paired with the prompt.

6. The system of claim 5, wherein the advertisement is loaded to the remote prompting host.

7. The system of claim 6, wherein the remote prompting host is configured to:
determine if the advertisement is paired and sent with the prompt based on the event,
send the advertisement with the prompt, and
notify a central server responsible for the advertisement that the advertisement was sent and displayed at the first network of the user.

8. The system of claim 1, wherein the bridge device includes a Transducer Access Point (TAP) device configured to bridge wireless communication between the sensor and the remote prompting host, wherein the TAP device is configured to support wireless communication based on a plurality of communication protocols including short-range communication protocols and Ethernet.

9. A method comprising:
collecting data related to an event associated with a user by a sensor operable on a first network, wherein the sensor is configured to support a first wireless protocol operational in sub-gigahertz frequency range providing a data rate of upto 100 kbps;
bridging wireless communication based at least on the first protocol at the sensor and wireless communication based at least on an Ethernet protocol at a remote prompting host;
receiving, from the sensor at the remote prompting host, the data collected by the sensor, wherein the remote prompting host is operable on a second network and includes one or more hardware modules;
processing, by the one or more hardware modules, the data collected by the sensor based on a probabilistic model to identify the event;
based on the event identified based on the received data and a predefined rule, generating and transmitting, by the one or more hardware modules, a prompt related to the identified event, wherein at least first and second prompts, the first and second prompts each including information about the identified event and an action responsive to the identified event;
receiving the first prompt from the remote prompting host;
presenting the first prompt to the user via a physical device associated with a remote prompting client operable on the first network; and
receiving a second prompt from the remote prompting host notifying another user that the user has received the prompt associated with the identified event.

10. The method of claim 9, wherein the sensor is located within the first network.

11. The method of claim 9, wherein the remote prompting client is associated with at least one of a television, phone, cell phone, picture frame display, and mirror on the first network.

12. The method of claim 9, wherein the prompt is at least one of a message, image and sound.

13. The method of claim 9, wherein an advertisement is paired with the prompt.

14. The method of claim 13, wherein the advertisement is loaded to the remote prompting host.

15. The method of claim 14, wherein the remote prompting host is configured to:
determine if the advertisement is paired and sent with the prompt based on the event,
send the advertisement with the prompt, and
notify a central server responsible for the advertisement that the advertisement was sent and displayed at the first network associated with the user.

16. A system comprising:
a sensor arranged in a first network and configured to collect data related to an event that occurs in the system, wherein the sensor is configured to support a first wireless protocol operational in sub-gigahertz frequency range providing a data rate of upto 100 kbps;
a computing device operable on a second network and comprising one or more hardware modules configured to:
receive, from the sensor, the data collected by the sensor; and
based on the event based on the received data and a predefined rule, generate and transmit a prompt related to the identified event, wherein the prompt includes information about the identified event and an action responsive to the identified event;
a first prompting device arranged on the first network and configured to receive the prompt from the computing device and display the prompt to a user via a physical device associated with the first prompting device;
a second prompting device arranged on the second network and configured to receive a notification from the remote prompting host and present the notification to another user, the notification indicating at least that the user has received the prompt associated with the identified event; and
a gateway operable on the first network and the second network and configured to bridge wireless communication based at least on the first protocol at the sensor arranged in the first network with wireless communication based at least on an Ethernet protocol at the computing device in the second network.

17. The system of claim 16, wherein the gateway is configured to bridge wireless communication between the sensor and the computing device, wherein the gateway is configured to support wireless communication based on a plurality of communication protocols including short-range communication protocols and Ethernet.

18. The system of claim 16, wherein the sensor is configured to collect at least physiological data, biological data and/or environmental data related to the user.

\* \* \* \* \*